US012232861B2

(12) United States Patent
Strano et al.

(10) Patent No.: US 12,232,861 B2
(45) Date of Patent: Feb. 25, 2025

(54) APPARATUS AND METHOD FOR PASSIVE MARKERS LOCALIZATION WITHIN A BODY

(71) Applicant: SPRINGLOC LTD., Jerusalem (IL)

(72) Inventors: Shalom Strano, Jerusalem (IL); Alexander Lomes, Moshav Hosen (IL); Steve Krupa, Haifa (IL)

(73) Assignee: SPRINGLOC LTD., Jerusalem (IL)

( * ) Notice: Subject to any disclaimer, the term of this patent is extended or adjusted under 35 U.S.C. 154(b) by 280 days.

(21) Appl. No.: 17/841,663

(22) Filed: Jun. 16, 2022

(65) Prior Publication Data

US 2023/0011384 A1 Jan. 12, 2023

Related U.S. Application Data

(63) Continuation-in-part of application No. 17/724,487, filed on Apr. 19, 2022.

(60) Provisional application No. 63/218,973, filed on Jul. 7, 2021.

(51) Int. Cl.
*A61B 5/06* (2006.01)
*A61B 90/00* (2016.01)
*A61B 90/98* (2016.01)

(52) U.S. Cl.
CPC .............. *A61B 5/064* (2013.01); *A61B 90/39* (2016.02); *A61B 90/98* (2016.02); *A61B 2090/3929* (2016.02); *A61B 2090/3945* (2016.02); *A61B 2090/3966* (2016.02); *A61B 2090/3983* (2016.02)

(58) Field of Classification Search
CPC . A61B 90/39; A61B 90/98; A61B 2090/3929; A61B 2090/3945; A61B 2090/3966; A61B 2090/3983; A61B 5/064
See application file for complete search history.

(56) References Cited

U.S. PATENT DOCUMENTS

| 9,713,437 | B2 | 7/2017 | Fullerton et al. |
| 10,154,799 | B2 | 12/2018 | van der Weide et al. |
| 10,827,949 | B2 | 11/2020 | Greene et al. |
| 10,849,529 | B2 | 12/2020 | Brander et al. |

(Continued)

OTHER PUBLICATIONS

Hologic Inc ("LOCalizer"): https://hologicbreastsurgery.com/en/portfolio/localizer-wire-free-guidance-system/.

(Continued)

*Primary Examiner* — Chao Sheng
(74) *Attorney, Agent, or Firm* — Smith Tempel Blaha LLC; Gregory Scott Smith

(57) ABSTRACT

A system for localizing a region of interest (ROI) within a patient's body is disclosed. An embodiment of the system may comprise a pad that can be placed in association with the patient's body; one or more markers which are placed within a patient's body in association with the ROI, each marker being associated with one or more antennas and a unique collective ID; a locator comprising one or more antennas for transmitting/receiving a microwave (MW) signal into/from the patient's body in order to identify the one or more markers and a processing unit that is configured to control the operation of the system and for determining the distance from the locator to each one of the one or more markers.

36 Claims, 10 Drawing Sheets

(56) References Cited

U.S. PATENT DOCUMENTS

2018/0279907 A1* 10/2018 Greene ................ H01Q 1/002

OTHER PUBLICATIONS

FCC table of frequency allocations 01.02.2021.pdf.
"Measurement of the penetration depths of red and near infrared light in human "ex vivo" tissues", in Journal of Photochemistry and Photobiology B: Biology, 2000.
"Optimization of output power and transmission efficiency of magnetically coupled resonance wireless power transfer system" by R. Yan, X. Guo, S. Cao and C. Zhang, on-line published Feb. 1, 2018.
https://cdn-shop.adafruit.com/productfiles/4034/P4034_datasheet_NTAG_203.pdf.
"A 60GHz Analog Phase Shifter in 65nm Bulk CMOS Process" by S. Harrison, Z. Ping, IJCNC Jul. 2010.

* cited by examiner

FIG. 1A
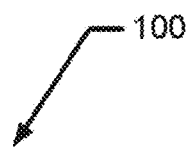
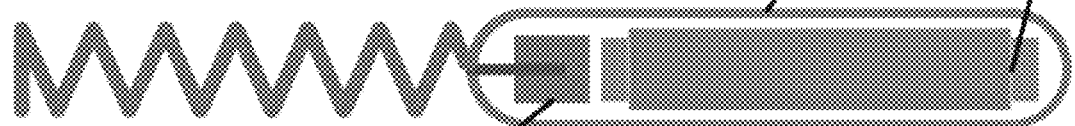
FIG. 1B
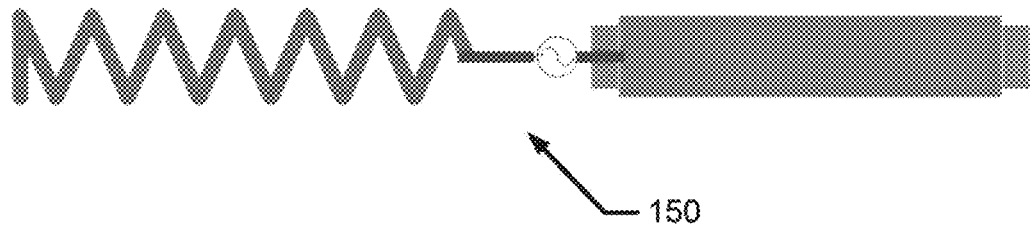
FIG. 1C

APPARATUS AND METHOD FOR PASSIVE MARKERS LOCALIZATION WITHIN A BODY

CROSS-REFERENCE TO RELATED APPLICATIONS

This utility patent application is being filed in the United States as a non-provisional application for patent, claiming the benefit of the prior filing date under Title 35, U.S.C. § 119(e) of the U.S. provisional application for patent that was filed on Jul. 7, 21 and assigned the Ser. No. 63/218,973, and this utility patent application is also a continuation-in-part of United States non-provisional application for patent that was filed on Apr. 19, 22 and assigned the Ser. No. 17/724,487. These applications and the applications they incorporate by reference are all incorporated by reference herein in their entirety.

FIELD OF THE DISCLOSURE

The present disclosure relates to the field of localization of one or more passive RF markers implanted or placed into the human body, for the purpose of mapping in-vivo body regions of interest (ROIs) accurately, in order to facilitate further pathological, diagnostic, surgical or therapeutic procedures.

BACKGROUND

A common and serious challenge in many medical instances is the accurate localization of sites and or lesions requiring monitoring or treatment such as but not limited to their surgical removal. After imaging of a body tissue, whether by mammography, ultrasound, Magnetic-Resonance-Imaging (MRI), Computed-Tomography (CT) or any other imaging system, there may be a need to mark one or more regions of interest (ROI). The ROI can be a foreign body, suspected tumor, or other lesion, etc. Marking the ROI is needed in order to inform medical personnel about the tissue site(s) which may require further examination/s or subsequent treatment such as but not limited to surgery. The marking of the ROI is not site specific and may be applicable in anatomical sites such as for example but not limited to the breast, lung tissue, soft tissues, lymph nodes etc.

A number of different types of passive RF marker systems currently exist in the market. Passive RF markers are tiny electronic devices enclosed within bio-compatible casings. The "passive" nature of the marker means it does not have any persistent on-board source of energy for its operation, but rather receives this energy remotely from some external source. Another common property of such markers is the use electromagnetic waves (RF signals) for estimating the distance between said markers and some hand-held or machine or robotic operated device controlling the marker localization process. Different names are used to describe this device i.e., hand held locator, reader, locator, probe, etc. The term hand-held locator will be generally used and understood to include all forms of localization device including robotic, machine, endoscopically etc. operated localization devices.

The RFID marker system of the Health Beacons Inc. (U.S. Pat. No. 10,849,529B2), or Elucent Medical Inc. (U.S. Pat. No. 10,154,799B2), or "LOCalizer" of Hologic Inc (https://hologicbreastsurgery.com/en/portfolio/localizer-wire-free-guidance-system/) are examples of previous art of passive RF markers. These markers have ferrite-based magnetic antennas providing RF coupling with the source antenna residing within the hand-held locator of the system. In general, RFID markers relay RF signals modulated by ID codes which are received by the hand-held locator. This kind of signal permits distance estimation based on the signal amplitude(s) received by the hand-held device. The conventional (low) RF frequencies (i.e., FCC approved band at 134 KHz) used for power transfer between the hand-held locator and the marker do not account for dielectric loss mechanisms in the tissue. Reductions in signal amplitude are assumed to depend exclusively on distance via the inverse square law. This property allows for estimation of the distance between the marker and locator by simply measuring the amplitude of the signal received by the locator.

In reality, the human body (particularly the internal tissue environment of the breast) is not homogeneous and has dielectric loss mechanisms. Blood vessels, malignant tissues and hematomas are some examples of tissues having significant conductivity, thus compounding the expected inverse-square signal amplitude reductions with significant dissipative losses. Another disadvantage of RFID marker systems is the sensitivity of localization accuracy and repeatability dependent on the spatial orientation of the locator relative to the markers. The energy harvesting as well as the coded response of the markers work effectively only in scenarios wherein the magnetic antennas of the marker and the locator are coaxially aligned. Small angle variations as well as axis displacement lead to disruption of localization.

An additional significant problem of using current RFID markers in existing medical treatment workflows is the material composition of the magnetic antennas. The reliance on magnetic materials (ferrites) in current systems stems from the use of a relatively weak wireless energy power source: ie, the hand-held locator. Due to the low frequency of the RF energy transfer waveform, the small size of the antenna within these devices cannot wirelessly couple enough power to the markers without the assistance of a strongly magnetic material (e.g. ferrite) within the core of each markers antenna. Unfortunately, this ferrite material is incompatible with existing MRI requirements and creates huge artifact on the MRI image.

Another method of passive RF marker localization is the SAVI SCOUT marker system of Cianna Medical Inc. (U.S. Pat. No. 9,713,437B2). This marker system is based on a micro-impulse radar (MIR) concept of distance estimation by measuring the double ("there-and-back") propagation delay of an Ultra Wide Band (UWB) pulse launched by the hand-held locator (probe). After some unperturbed propagation within the interposed tissue layers, this pulse interacts with the marker, and the subsequent reflected waveform is captured by appropriately tuned receiver circuitry within the locator (probe). This system uses a microwave signal of the range of 5.8 GHz (FCC approved band for medical applications). The marker of SAVI SCOUT is activated (via external energy harvesting) from an infra-red (IR) external source located at the tip of the hand-held device. The high propagating losses of IR in human (breast) tissue require some form of IR focusing mechanism, reducing the effective angle of the locator view. In general, this method of marker excitation, combined with the relatively low reflectivity (Radar Cross Section, RCS) of the marker antenna (a half-wave dipole) creates some disadvantages, such as limited depth of marker detection and the need for an exacting, skill-dependent "directional search" by the operator, ie, poor discrete discrimination of closely placed markers. The presence of hematoma can severely disrupt and complicate the marker localization process. These markers notably lack an electronic ID.

A more recent SAVI SCOUT development (U.S. Pat. No. 10,827,949 B2) discloses another approach of distance estimation on the basis of a CW radar concept. In this approach, IR pulses not only provide energy for marker operation, but also provide an encoded excitation of the markers, permitting a "logical" (discriminatory) identification of the marker response. In spite of employing a tip-mounted, hemispheric pattern MW antenna in the latest generation of the Scout locator (probe), the IR excitation still requires a stringent, "orient the probe toward the marker" operational approach. As such, two limitations of the SAVI SCOUT marker system remain unchanged: a limited depth of marker detection and a limited view angle (effective field of view) of the probe. As the probe scans closer to the marker of interest, it loses "sight" (wireless connectivity) with the other markers implanted within the same region of the body. The limited depth of marker detection is a result of the low depth-of-penetration (DOP) of IR energy into human tissue of about 4 mm. (see "Measurement of the penetration depths of red and near infrared light in human "ex vivo" tissues" in Journal of Photochemistry and Photobiology B: Biology, 2000). At a proclaimed operative depth of 60 mm (within breast tissue) or 3 mm of hematoma, the IR energy losses are about 65 dB, or ~3000000 times.

A fundamental requirement of markers is that they should not migrate from the site of their original placement. ie, they should remain closely associated with the ROI which they are assigned to localize. For example, they should not move on compression of breast tissue for example at mammography or at the time of surgery. Antennas extending beyond the body of the marker assist in the fixation of the markers in vivo. Current RFID markers without external antennae are prone to migration.

Accordingly, these systems and their markers have limitations. The following are examples of such limitations. The examples are cited to illustrate the overall deficiencies currently encountered in the general clinical setting and are not all applicable to each individual system. The limitations include: Poor detection performance at distances deep to the skin. Poor detection in the presence of hematomas and fluid collections. MRI bloom artifacts which are especially important in patients undergoing neoadjuvant therapy where markers are placed pre therapy and therapy success is monitored with follow-up repeat MRI studies with markers still in vivo. In cases where a plurality of markers have been placed and particularly when placed close to each other, it is difficult to discretely localize and differentiate between differing individual marker identities. In instances where more than one marker has been placed in a single anatomical region, for example in one breast, current systems' markers lack sufficient identification criteria to uniquely characterize and differentiate each marker from other markers of the same and different systems as seen on imaging systems such as mammography. Some systems have markers without any electronic ID. Current systems are generally underpowered for the localization of ferrite free markers.

Accordingly, further apparatus and methods for the designation and localization of foreign bodies, lesions or other tissue structures in order to facilitate further pathological, diagnostic, surgical or therapeutic procedures are needed and would be useful.

SUMMARY

The needs and the deficiencies described above are not intended to limit the scope of the inventive concepts of the present disclosure in any manner. The needs are presented for illustration only. The disclosure is directed to a novel technique for localizing one or more markers within a patient's body, for example but not limited to the breast, lung, lymph nodes, soft tissues etc.

The disclosed technique is an integrated, multi-component wireless system providing for accurate marker localization for example during surgical procedures. The system is designed to accurately estimate the electromagnetic propagation delays of modulated RF signals transmitted by one or more markers placed, attached to or implanted (for example via a needle, robot, endoscope, laparoscope etc.) into or in the area of the ROI(s) and activated by a RFID code signal. The propagation delay can be estimated by measuring the phase shift of the signals. The disclosed technique allows the surgeon to individually track each one of the implanted markers providing the ability for more accurate delineation and removal of the surgical ROI(s). The markers can also be used to uniquely identify lesions requiring targeted follow up observation or targeted therapy.

The disclosed system may comprise one or more pads, one or more markers, a handheld reader (a locator) and a processing unit. A reader who wishes to learn more about the markers is invited to read the non-provisional application for U.S. Ser. No. 17/724,487, which is incorporated herein by reference in its entirety. The pad may comprise a magnetic loop antenna, which may be greater in size than the breast area of a patient. The antenna can be connected to electronic circuitry that provides signals to be transmitted via the antenna. The antenna generates the electromagnetic near field that can cover an entire body anatomical volume for example a breast. The antenna, the electronic circuitry and a local energy source (such as but not limited to a battery) are enclosed in the pad. Alternatively they may be enclosed in a form other than a pad.

The term pad is understood to include other physical shapes and forms containing the antenna, the electronic circuitry and a local energy source and the term is used generally. The pad can be placed in association with the patient for example on the surgery table below the patient's body and is configured to transfer power to all implanted markers within the spatial region of the antenna. In the following description and claims, the terms processing unit, a handheld personal computer, a tablet computer, a personal digital assistant (PDA), a smartphone, etc. may be used interchangeably and the term tablet can be used as a representative term of this group.

In one embodiment, the marker can comprise an energy harvesting module and transferring subsystem. The marker can act as a transponder. The electromagnetic near field covers the region of interest (ROI) of the patient's body with one or more markers implanted within it. The field pad provides enough energy for marker operation including the powering of MRI compatible ferrite free markers. Additionally, the signal generated by the pad provides synchronization of the entire system and is used for coherent measurement of the signal phase difference required for temporal delay estimation of the wave propagating between marker and hand-held locator. The frequency of the carrier signal generated by the pad is low enough to ensure near field coverage of the ROI, ie, the spatial portion within the patient's body including the implanted marker/s. In the present disclosure and the claims, the terms: pad, excitation field pad, excitation pad, or field pad may be used interchangeably.

In another embodiment the excitation field pad uses code modulation of its carrier signal for identification and subsequent activation of the user-selected marker. For this purpose, the marker comprises the circuitry for the demodulation and decoding of the signal sent by the excitation pad. In case of a code match (henceforth referred to as coincidence) with the ID code stored in the marker's memory, the marker is activated and ready to respond to the test signal sent by the hand-held locator.

In another embodiment the hand-held locator receives the synchronization signal from the excitation pad and uses it for generating a test signal for irradiation towards the marker/s located (implanted or placed) within the patient's body. This test signal uses a much higher (preferably Microwave, MW) carrier frequency than the signal generated by the pad. The frequency of this test signal from the end-fire antenna located at the small tip of the hand-held locator allows for efficient signal radiation. This antenna has a wide transmitting/receiving pattern covering the markers in the ROI. Additionally, the wavelength of this frequency, propagating inside the tissue of the patient's body, allows for the size (length) of the marker's MW antenna to comprise a significant fraction of the test signal wavelength, while meeting the operational requirements for a reduced physical size of the markers. The overall physical length of a marker (including the external antenna part) can be less than 12 mm, while the length of the marker capsule can be less than 7 mm.

The test signal transmitted by the hand-held locator towards the implanted marker/s is composed of two side-band frequency components symmetrically deployed around a central MW frequency, without the central frequency component itself. The side-band components are created via double-balance modulation of a MW carrier, combining a pure CW microwave tone generated by the locator's on-board oscillator with the synchronization signal received from the pad. This signal propagates into the patient's tissue and reaches the MW antenna of the activated marker. Only an activated marker, whose internal ID code is coincident with the user-selected code transmitted by the pad, is able to respond to the MW test signal emanating from the hand-held locator.

The marker uses a portion of the harvested energy to change the spectrum of the incident MW test signal, amplifying it and transmitting this new signal back toward the hand-held locator. This new signal is the result of double-balance modulation of the received MW test signal and the synchronization signal coming from the pad. The spectrum of this new signal transmitted by the marker is composed of a central MW carrier tone plus two symmetrically deployed side-band components, relaying signal information from the second harmonic of the lower-frequency synchronization signal.

The signal transmitted (transponded) by the excited marker reaches the MW antenna of the hand-held locator. The phase of its side-band components is proportional to the double time delay of the MW propagating between the locator and the marker. In another embodiment, the electronic components within the locator perform the phase difference measurement between the detected signals coming from the excited marker and the reference synchronization signal received from the excitation pad. The value of this phase difference is converted into digital form and transferred to the tablet computer via Bluetooth (or similar) interface for distance estimation calculations.

The process of marker localization begins with placement of the tip of the locator in the vicinity of the marker/s location. The locator tip may be placed on the skin of the breast or other appropriate body tissue containing the marker/s, for example lung tissue. Orientation of the locator in the precise direction of the marker is not required, owing to the wide field pattern of the MW antenna built into the locator tip. After issuing the start command, the tablet may instruct, via Bluetooth, the pad to emit an excitation electromagnetic field. Simultaneously the Tablet Computer sends (via Bluetooth interface, for example) the marker/s ID code/s to the excitation Source Pad, located adjacent to the patient.

The excitation pad initiates a sub-routine for coded excitation of the region of interest and the hand-held locator sends the MW test signal into the body. Every code coincidence in every marker in the locator's "field of view" triggers a distance measurement between the locator and the appropriate, user-selected marker. The list of distances to all "visible" markers as well as their ID codes is displayed on the screen of the tablet computer. The distance to the closest (currently selected) marker is presented as an acoustic signal generated by the tablet computer. The pitch of this audio signal increases in response to a reduction in the estimated locator-to-marker distance. As the operator (surgeon) slides the tip of the locator on for example the patient's skin, the pitch changes. The pitch reaches an extremal value when the locator's tip reaches the minimal distance to the marker (the point of closest proximity). The operator can toggle acoustic monitoring to another marker by issuing the command "change marker", by means of a simple man-machine interface (MMI). This procedure can be repeated sequentially, ultimately resulting in localization of all markers within the region of interest.

In another embodiment, the locator comprises the built-in XYZ IMU (Inertial Measurement Unit—for example, commercial MPU9255) providing real-time displacement measurement of any movement of the locator. This information is relayed to the tablet computer, permitting visual tracking of the locator's real-time trajectory. The simultaneous measurement of the locator-to-marker distance, paired with the locator's movement trajectory, enables visual feedback concerning "correct" or "wrong" directions of the search (locator tip scanning) for the currently selected marker. Information about the "correct" search direction for the locator is indicated by topologically activating a group of LEDs arrayed around the circumference of the locator wand. This locator-based feedback provides additional information for the surgeon, and greatly expedites the marker localization process.

In another embodiment, the finding of the depth (minimum distance) of each one of the in vivo implanted markers together with the estimation of distance between markers creates a system of 3D coordinates of the group of markers relative to the first detected marker. These coordinates can be used by the system computer for the generation of a wire-formed 3D object of the implanted markers' group in the computer memory. This object can be further used for displaying marker location information to the surgeon in real-time.

In another embodiment, the marker comprises a dual band antenna permitting harvesting of the energy generated by the excitation pad (at a lower RF frequency) coincident with reception of the MW test signal launched by the locator. Following decoding, the marker generates a different MW signal and transmits with minimum-latency the different MW signal back to the locator.

An example embodiment of a marker may comprise a microelectronic chip which stores a unique electronic ID, a dipole antenna and an electromagnetic antenna, a hermetic bio-compatible container, and unique visual ID (VID) symbols/s. In some examples of the marker an external identifying element (EIE) can be attached to the hermetic biocompatible container. In such embodiment, the EIE is not electrically connected to the microelectronic chip. The components of the marker can be comprised of non-ferrite material and can be MRI compatible without a bloom artifact.

In some embodiments of the marker, the visual ID (VID) of the marker/s can be designated by varying uniquely identifiable radio opaque identification markings. Markings can be such as but not limited to shapes, letters or numbers on or within the receptacle capsule of the marker. In some embodiments of marker, the VID of the marker/s can be designated by unique ridges on the markers surface, unique interspaced gaps in the markers metallic coil windings and attached rings and clips for example (not shown). In some embodiments of marker, the VID of the marker/s can be designated by varying the physical appearance or geometric bended shape of the marker and or the geometric bended shape of an element, which can be an external antenna and/or an external identifying element (EIE), which are attached to the container.

For example, the external antenna can be in the shape of a spring or hook (which can deploy on placement of the marker) or clip or ring etc. The VID of each marker can be established by at least one feature from a group of features including for example; the marker body shape or form, radio opaque markings, antennae shape (for example as a spring), the shape of an attached EIE, unique ridges on the markers surface, unique interspaced gaps in the markers metallic coil windings and attached rings and clips. The above types of VID can be uniquely visible with imaging modalities such as but not limited to X-Ray, mammography and ultrasound.

Furthermore, the VID of the markers can be combined with their electronic identification. The combination of the VID with the unique electronic ID of each individual marker constitutes the unique collective ID of that marker. For example, a specific marker visualized on a mammogram X-Ray can be identified by the unique radio opaque markings of its encasement and by the unique shape of its external antenna and or its EIE as well as by its unique electronic ID that was stored in the microelectronic chip prior to its placement in the body tissue. All the forms of ID designation of each marker can be correlated and combined so as to characterize each marker's unique collective ID.

In some embodiments, the low frequency part of the antenna is fully resided inside the hermetic capsule of the marker, while a part of MW antenna is extended externally from the marker body. The capsule and external features of the marker device are built from biocompatible materials. For example, the hermetic capsule can be comprised of glass, plastic or silicone or a combination of biocompatible materials. The antennae or external components can be comprised of for example tungsten and/or dyneme or nitinol.

Two markers can be mechanically connected by their external protruding features for example by their interconnecting spring antennae. The connecting antennae can be comprised of tungsten or polymeric wire. Owing to the mechanical properties of pre-bent tungsten or polymeric wire, a pair of markers having a common pre-bent spring connection can effectively act as a post-deployment anchor, preventing migration of this marker pair. Similarly, the external spring antenna and EIE's can stabilize markers in vivo and prevent marker migration.

The foregoing summary is not intended to summarize each potential embodiment or every aspect of the present invention, and other features and advantages of the present invention will become apparent upon reading the following detailed description of example embodiments with the accompanying drawings and appended claims.

Furthermore, although specific embodiments are described in detail to illustrate the inventive concepts to a person skilled in the art, such embodiments can be modified to various modifications and alternative forms. Accordingly, the figures and written description are not intended to limit the scope of the inventive concepts in any manner.

Other objects, features, and advantages of the disclosed apparatuses will become apparent upon reading the following detailed description of example embodiments with the accompanying drawings and appended claims.

BRIEF DESCRIPTION OF THE DRAWINGS

Exemplary embodiments of the present disclosure will be understood and appreciated more fully from the following detailed description, taken in conjunction with the drawings in which:

FIG. 1A shows a first view of an example embodiment of a dual-Band antenna transponder marker or tag that may be implanted or placed within patient's body;

FIG. 1B shows a second view of an example embodiment of a dual-Band antenna transponder marker or tag that may be implanted or placed within patient's body;

FIG. 1C shows a third view of an example embodiment of a dual-Band antenna transponder marker or tag that may be implanted or placed within patient's body;

DETAILED DESCRIPTION OF SOME EXAMPLE EMBODIMENTS

Turning now to the figures in which like numerals represent like elements throughout the several views, in which exemplary embodiments of the disclosed techniques are described. For convenience, only some elements of the same group may be labeled with numerals.

The purpose of the drawings is to describe examples of embodiments and not for production purpose. Therefore, features shown in the figures are chosen for convenience and clarity of presentation only and are not necessarily shown to scale. Moreover, the language used in this disclosure has been principally selected for readability and instructional purposes, and may not have been selected to define or limit the inventive subject matter.

In this specification, these implementations, or any other form that the invention may take, may be referred to as techniques. In general, the order of the steps of disclosed processes may be altered within the scope of the invention. Reference in the specification to "one embodiment" or to "an embodiment" means that a particular feature, structure, or characteristic described in connection with the embodiments is included in at least one embodiment of the invention, and multiple references to "one embodiment" or "an embodiment" should not be understood as necessarily all referring to the same embodiment.

In the following description, the words "unit," "element," "module", and "logical module" may be used interchangeably. Anything designated as a unit or module may be a stand-alone unit or a specialized or integrated module. A unit or a module may be modular or have modular aspects allowing it to be easily removed and replaced with another similar unit or module. Each unit or module may be any one of, or any combination of, hardware configured to execute the task ascribed to the unit or module. In the present disclosure the terms task, method, and process can be used interchangeably. In addition, the terms element and section can be used interchangeably.

In the following description, numerous details are set forth in order to provide a more thorough description of the system. It will be apparent, however, to one skilled in the art, that the disclosed system may be practiced without these specific details. In the other instances, well known features have not been described in detail so as not to unnecessarily obscure the system.

Figure 3:
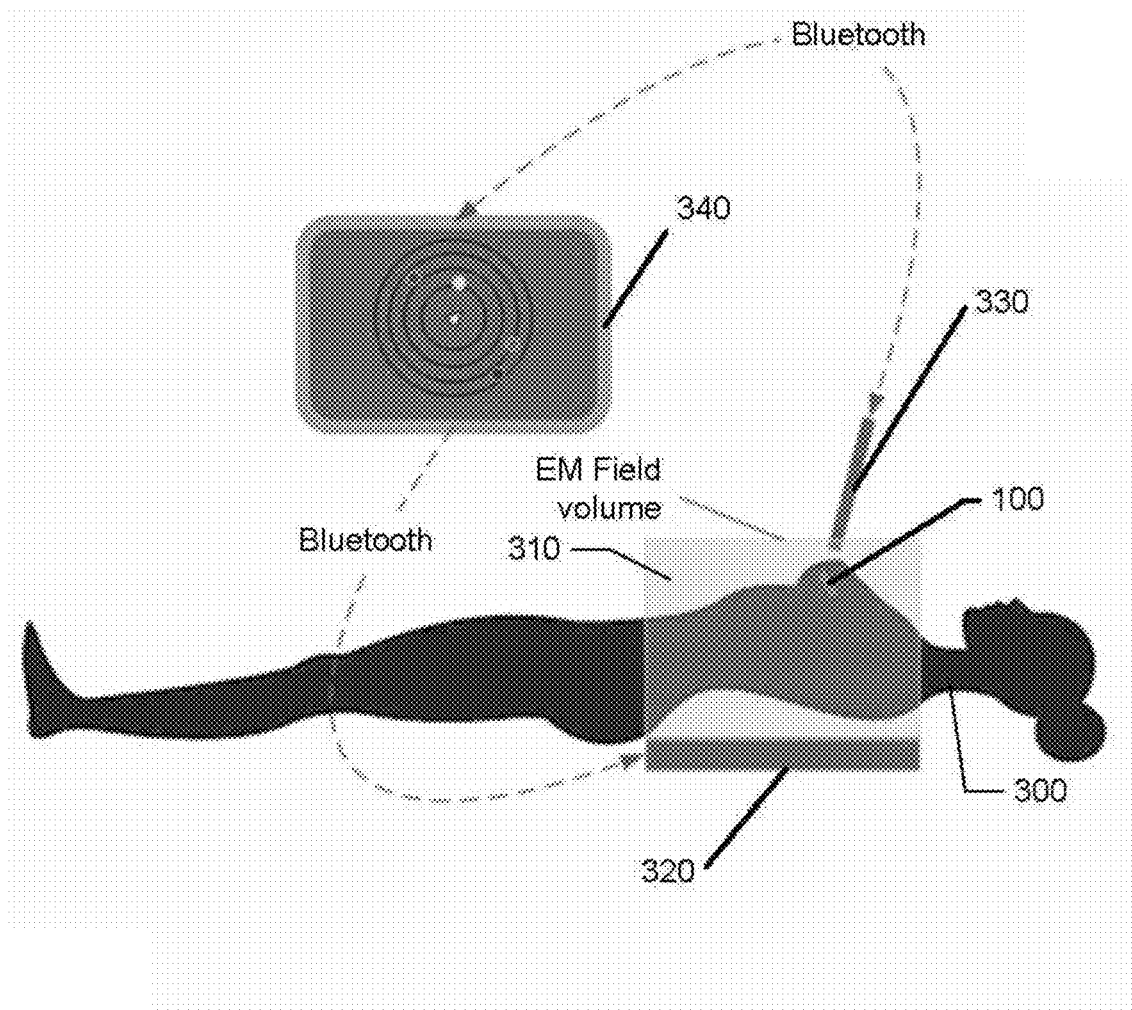
FIG. 3 Illustrates an example embodiment of the disclosed system concept.

The drawings FIG. 1A-1C show different views of an example embodiment of a transponder marker or tag 100 that may be implanted or placed within patient's body such as within a breast 300 as shown in FIG. 3, for example by a delivery system like a needle assembly (not shown here). Generally, the marker 100 comprises a microchip 110, including all electronic components, magnetic antenna 120 and internal part of microwave antenna 130a enclosed into hermetic bio-compatible case 140. The marker has additionally the external part 130b of the microwave antenna. The components of the marker can be made of non-ferrite material and can be MRI compatible without a bloom artifact.

In an example embodiment, the magnetic antenna 120 may be a solenoid wired on a paramagnetic core like by not limited to glass. This antenna is tuned to the resonance frequency of an FCC approved for medical applications RF band of 13.56 MHz for the most efficient harvesting of electromagnetic energy irradiated by an excitation electromagnetic field pad 320 (see FIG. 3). The same magnetic antenna 120 structure can serve as a part (single arm) of the microwave dipole antenna 150 (FIG. 1B) working at another FCC approved band of 5800 MHz. At this frequency, the wired layer of the magnetic antenna 120 can be thought of as a solid conducting cylinder due to the commonly known skin effect, in conjunction with the low-impedance RF path established by the turn-to-turn capacitive coupling between neighboring turns/loops of the magnetic antenna solenoid. This conducting cylinder together with the internal part 130a of the dipole antenna and external part 130b of the dipole antenna creates the half-wave resonant dual band antenna 150.

Figure 2:
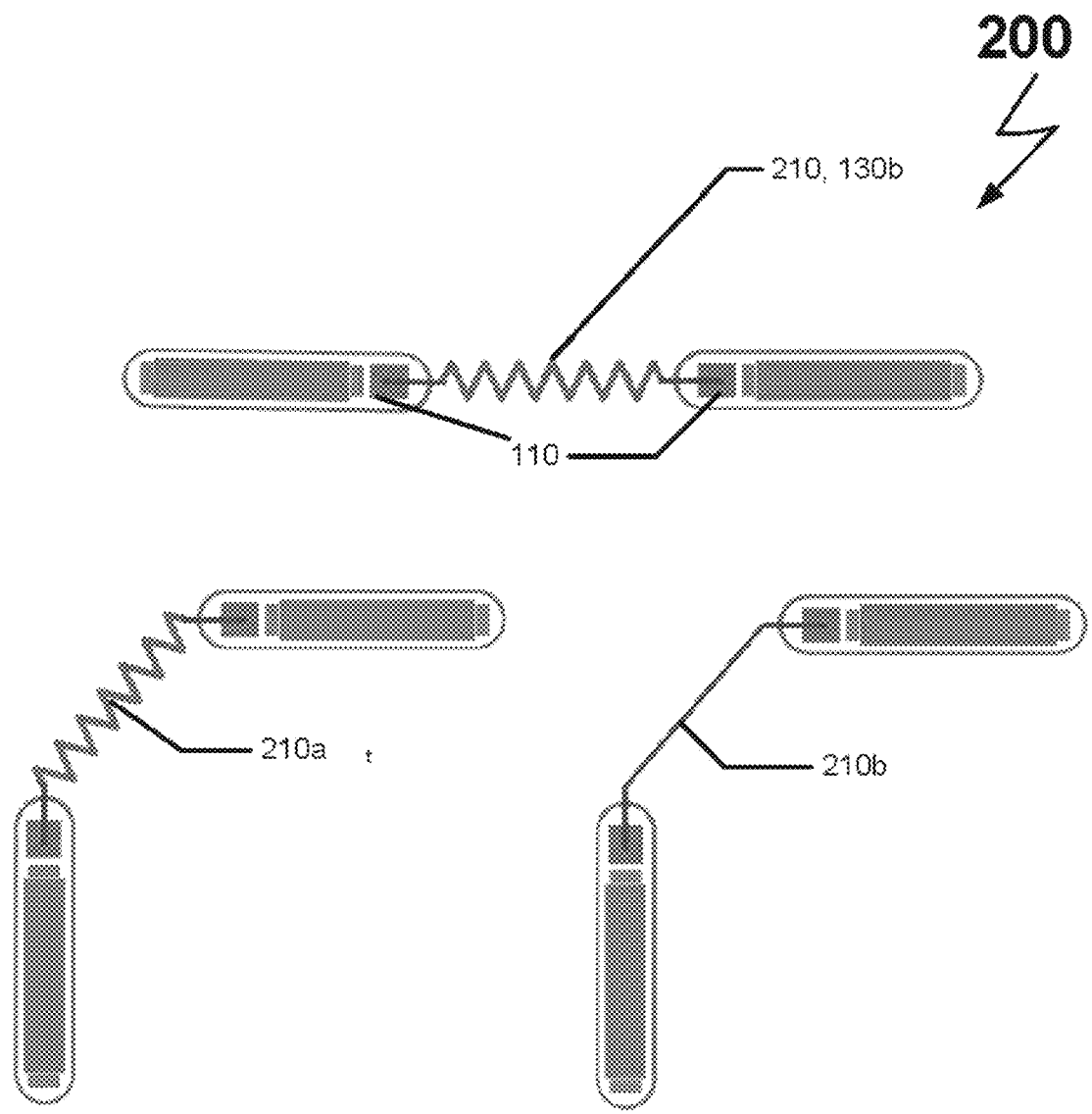
FIG. 2 depicts different embodiments of marker pairs, illustrating the assembly concept.

In an example embodiment, the external part of the microwave antenna 130b can serve as an anchor preventing the migration of the marker after implantation/placement into soft tissues. The antenna can be comprised of memory metals. The antenna can be in the form of a spring or some other visually identifiable configuration. EIE's and VID's can be associated with the marker (not shown). The effect of self-anchoring can be improved by connecting two markers by their external parts, for example, by the connection of the 130 microwave antennas (see FIG. 2). The common connecting part of marker pair 210 can be built from bio-compatible metals like but not limited to tungsten or nitinol and can have spring properties. So-called memory metals can be used.

Assuming the activation of each marker is performed sequentially at different and independent time intervals, the marker electronics 110 activate the microwave antennas of each marker of the pair independently, without interference of operation of each marker of the pair. Different types of spring connections between marker pairs can be used depending on surgical requirements. The expandable pre-bent spring 210a can be used for example in case of heterogeneous tissue. The fixed spring 210b can be used for example in case of homogeneous soft tissue.

In an example embodiment, the passive marker 100 is part of a system for localizing marker/s implanted within a patient's body, see FIG. 3. The system comprises the excitation electromagnetic (EM) field pad 320, creating the EM field penetrating the volume of interest 310, wherein the marker/s 100 have been previously implanted or placed. The system also comprises the remote hand-held locator 330, and the tablet computer 340 providing general control and monitoring of entire system. The locator can also be machine, robotic endoscopically, laparoscopically etc operated.

In an example embodiment, the marker 100 harvests the electromagnetic energy within the volume 310 of the ROI from the external excitation field source pad 320 and simultaneously responds to the MW test signal emanating from the hand-held locator 330. The signal (low-frequency carrier) generated by the pad 320 is modulated by a specific digital identification code. The process of ID activation of the marker can be achieved if and only if the code generated by the pad 320 matches the ID code stored in the selected marker's memory (within the chip 110). The user selected marker 100 is made active and is enabled to respond to the test signal sent from the locator 330.

Figure 4:
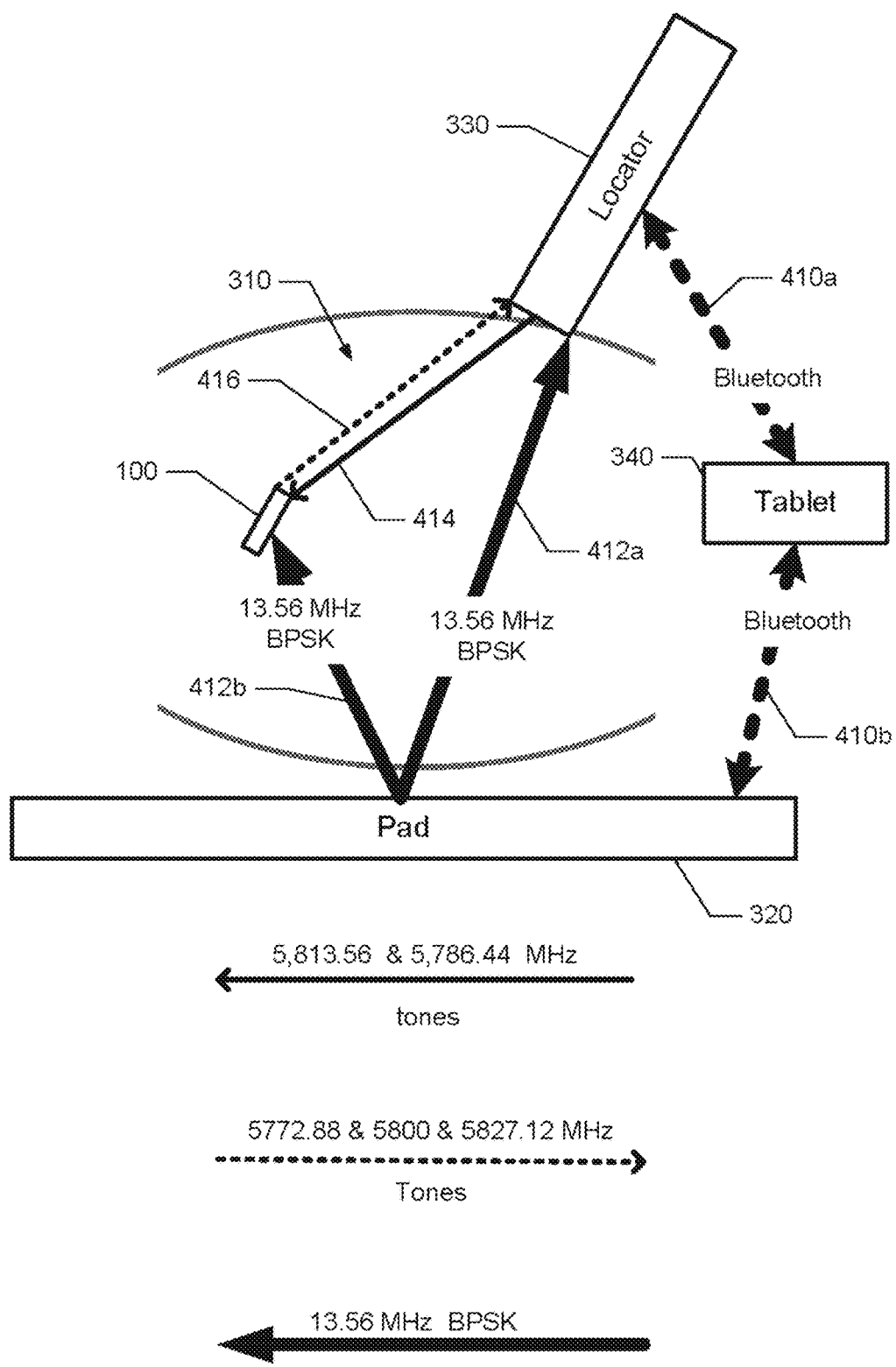
FIG. 4 Illustrates the RF signal paths schematic within the disclosed embodiment.

In FIG. 4, the external excitation field pad 320 creates an inductive field covering the volume of the region of interest 310 within the patient's body, providing enough energy for harvesting by a plurality of markers 100 within this volume. The signal has a carrier in the range of 13.56 MHz and is modulated by digital ID code using the binary-phase-shift-keying (BPSK) method.

Additionally, the carrier of this low-frequency RF signal is used as the synchronization signal in realizing the primary system function—coherent measurement of the selected marker's relative location (distance estimation). The BPSK modulation method provides maximum carrier signal power (maximum energy transference to the plurality of passive markers) and the simplest method of carrier recovery. This signal is received by magnetic antenna 120 of the marker (see FIGS. 1A, 1B and 1C) and is used by the passive marker for energy harvesting, ID demodulation, and decoding and generation of the MW response signal, which is triggered by reception of the MW test signal sent by the locator.

In the same example embodiment, the signal sent by the locator 320 and the response signal created by the marker 100 occupies the same FCC approved frequency band of 5800 MHz but have completely different spectra. For example, the test signal sent by the locator comprises two spectral components 5786.44 MHz and 5813.56 MHz, which represent balance modulated carrier of 5800 MHz by the first harmonic of the system synchronization signal of 13.56 MHz. The marker response is composed of the AM modulated signal having spectral components at 5772.98 MHz, 5800 MHz and 5827.12 MHz, which represent the carrier of 5800 MHz and two side-bands of the second harmonics of the synchronization signal (i.e., 27.12 MHz). This spectral difference allows using the excess energy harvested by the marker 100, for the amplification of the response signal transmitted toward the locator 330. The marker 100 uses the resonant half-wave dipole (microwave antenna) 150 for transponding interactions with the locator 330. Both antenna, one for energy harvesting and another for microwave interactions are combined in a dual-band antenna surrounding the marker electronics.

In the same exemplary embodiment, the Tablet computer 340 provides pre-operational monitoring and control of the hand-held locator 330 and the pad 320 by using the standard Bluetooth interface and protocol. During the surgery the hand-held locator 330 performs the phase measurements between the synchronization signal coming from the pad 320 and the response signal coming from the marker 100 which fundamentally encodes information about the distance between the locator 330 and the marker 100. Additionally, the locator measures the 3D acceleration of its movements (gliding) over the surface of the patient's skin. All this information is transferred to the computer 340 via Bluetooth IF for estimation of the plurality of marker locations.

Figure 5:
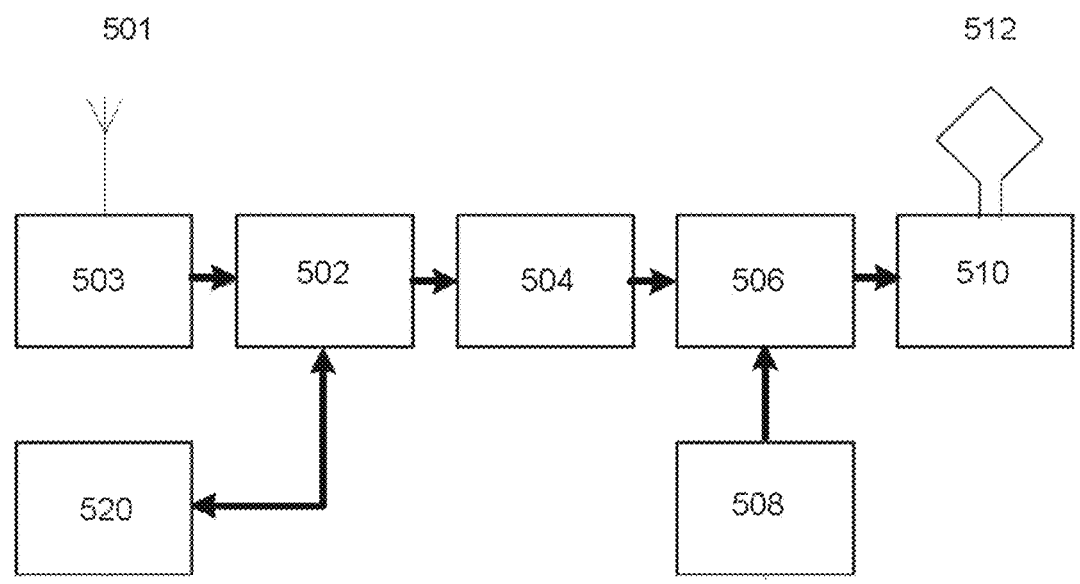
FIG. 5 Illustrates a potential embodiment of the Excitation field Pad, in block-diagram form.

In an example embodiment, the functional block diagram of the excitation electromagnetic field source pad 320 is illustrated in the FIG. 5. According to previous art ("Optimization of output power and transmission efficiency of magnetically coupled resonance wireless power transfer system" by R. Yan, X. Guo, S. Cao and C. Zhang, on-line published 2 Jan. 2018), the power transferred by a wireless coupled magnetic resonance system is proportional to the square of the radius of used coils. To fit within the confines of the small hand-held locator device, the prior art RF markers mentioned above use antennas with diameters less than 30 mm to excite the markers. The currently disclosed embodiment uses magnetic antenna 512 in the excitation pad of diameter (for example) 500 mm allowing significant (more than 270 times) amplification of the energy harvesting potential without modifying the marker geometry.

In such embodiment, the local controller 502 of the pad 320 receives via the Bluetooth link 503 (after the process of pairing) information regarding the one or more implanted markers within the region of interest. During each marker localization event in time, the local controller 502 commands the code sequence generator 504 to create a code sequence corresponding to the currently active code ID from the list stored in its memory. The code can be changed via a user-issued command into the tablet computer 340 (see FIG. 4). The code sequence is used as input by BPSK modulator 506 which modulates the carrier of the synchronization signal generated by crystal-controlled oscillator 508. The modulated signal is amplified by output power amplifier 510 and transmitted into the patient's body via magnetic loop antenna 512. This antenna generates the electromagnetic near-field which resonantly couples (via magnetic induction) to the plurality of markers' on-board magnetic antennas, ultimately providing operational power to the markers.

Figure 6:
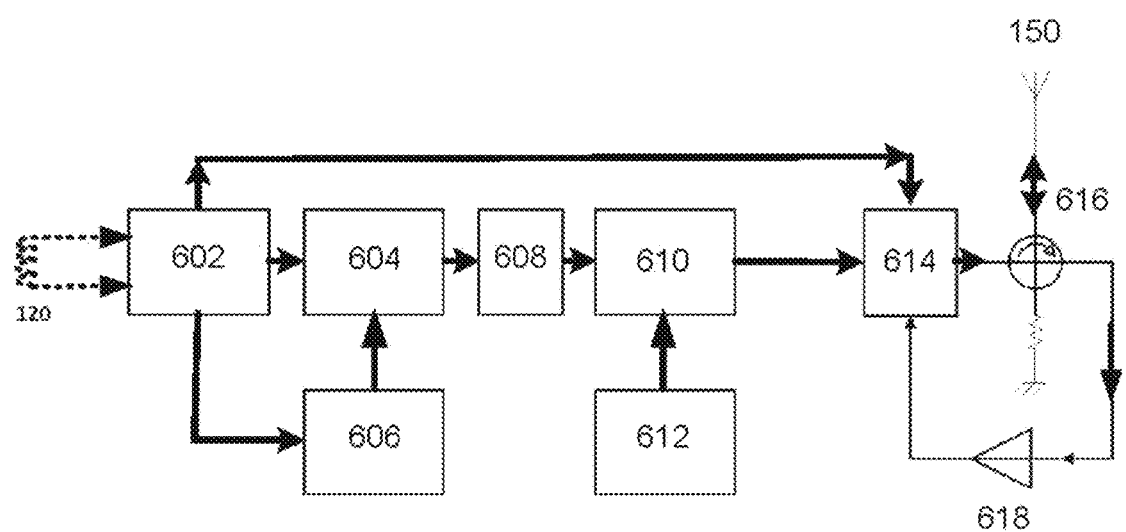
FIG. 6 Illustrates a potential embodiment of the marker's electronic systems, in general schematic form.

In an example embodiment, the functional block diagram of the microchip 110 (see FIGS. 1A, 1B and 1C) is illustrated in FIG. 6. This system-on-chip device can be a modification of an existing RFID chip, such as NTAG203 NFC (cdn-shop.adafruit.com/productfiles/4034/P4034_datasheet_NTAG_203.pdf). The blocks from 602 to 612 perform standard operations of the RFID system. The rectifier/local power supply 602 receives the signal from the markers magnetic antenna 120 and provides power supply energy for all electronic components of the marker 100. The AC components of this signal are used for PLL (phase-lock loop) 606 tuned to the carrier frequency of the receiving signal (low-frequency synchronization signal) and code demodulator 604. The output of this demodulator represents the code time sequence envelope similar to that generated by 504 (see FIG. 5). This signal is sampled by the local ND convertor 608 and in digital form is transferred to the local Processor/Correlator 610.

The correlator 610 uses the marker specific code ID stored in its memory 612 for decoding the processing code time sequence. In case of successful decoding (ID code match), the "code coincidence enable" signal is generated by the processor 610. The example embodiment of the chip extensions are represented by blocks 614, 616 and 618. The active circulator 616 (see previous art: "A 60 GHz Analog Phase Shifter in 65 nm Bulk CMOS Process" by S. Harrison, Z. Ping, IJCNC July 2010) receives the MW test signal coming from the hand-held locator 330. This signal has two spectral components of 5786.44 MHz and 5813.56 MHz of the FCC-permitted band 5800 MHz. These components are amplified by RF (LNA) amplifier 618 and are relayed to the Double-Balance Modulator 614.

In the case of a successful ID code match, the code coincidence enable signal generated by correlator 610 activates the modulator 614 to modulate (mathematical analog multiplication) the amplified MW signal received from the locator with the low-frequency AC signal coming from the pad. The result of this modulation is a signal having three spectral components in the 5800 MHz band, i.e., 5772.88 MHz, 5800 MHz and 5827.12 MHz. This signal is sent to the active circulator 616 and then transmitted via the same dipole antenna 150 of the marker. The spectral difference between the received and the transmitted signals prevent parasitic oscillations in RF Amplifier 618.

Figure 7:
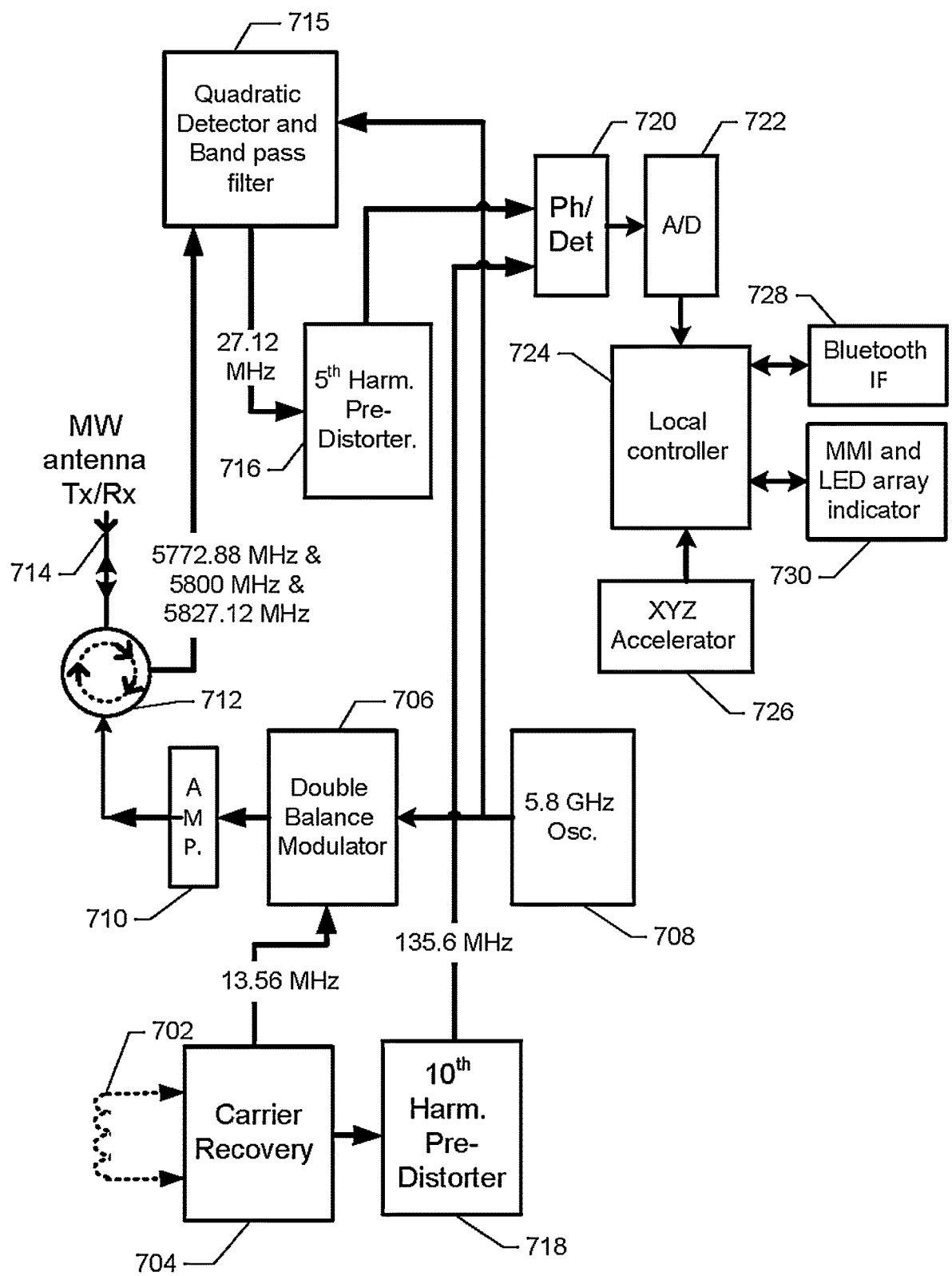
FIG. 7 Illustrates a potential embodiment of the electronic systems within the hand-held locator device, in block-diagram form.

In the example embodiment of the marker localization, the functional block-diagram of the locator 330 is illustrated in FIG. 7. The locator receives the synchronization signal from the pad 320 via magnetic antenna 702. This signal is passed to the carrier recovery circuitry to create a signal in the 13.56 MHz band, which is then used in generating the marker interrogation test signal. The pad signal ultimately serves as a reference signal for the phase difference estimation. The generation of the marker interrogation test signal is performed by modulation of the 5800 MHz carrier produced by oscillator 708 with the low-frequency 13.56 MHz signal coming from the carrier recovery circuit 704 (received from the pad 320).

The result of the Double-balance modulation 706 is a signal with two spectral components, occupying the 5786.44 MHz and 5813.56 MHz sub-bands. This signal is amplified by RF amplifier 710 and transmitted into the patient's body (toward the one or more implanted markers) via circulator 712 and microwave antenna 714. The same antenna 714 is used for receiving the active marker response. This response (microwave signal) contains 3 spectral components (i.e., 5772.88 MHz, 5800 MHz and 5827.12 MHz). This signal can be thought of as an amplitude modulated (AM) signal, with a modulating (envelope) waveform provided by the second harmonic of the synchronization signal 13.56 MHz. The modulation function is detected by detector 715, and passed through the band-pass-filter (BPF). The BPF is tuned to the required modulation function of 27.12 MHz (second harmonic of the synchronization signal 13.56 MHz). This modulation function contains the "there-and-back" (double-propagation) delay information associated with the microwave signals (centered at 5800 MHz) relayed from the locator 320 to the marker 100 and returned as a different, "response" signal. Accordingly, the harmonic signal at 27.12 MHz contains a scaled copy of the phase shift information (relative to some reference signal) of the fundamental frequency (13.56 MHz) signal.

Turning to the FIG. 7. In a "there-and-back", double propagation of the MW signal through (for example) 100 mm of human tissue, the harmonic signal of 27.12 MHz (detected by detector 715) does not vary more than 12 Deg in phase. This low measure of phase shift can be significantly increased through the employment of higher harmonics, created from the signals designated for the phase comparison. The pre-distorters 716 and 718 can be used for this harmonic signal generation, acting on the modulation envelope of the MW response and the RF synchronization signals, respectively. Using the 5th harmonic of the 27.12 MHz modulation envelope and the $10^{th}$ harmonic of the synchronization signal at 13.56 MHz permits phase comparison at 135.6 MHz, significantly improving the dynamic range of the phase detector 720.

The result of the phase different measurement is digitized by ND 722 and passed to the local controller 724. Simultaneously, the local controller 724 accepts the information regarding the position of the locator on the skin surface from the XYZ-Accelerometer 726. All this real-time information is transferred to the tablet computer 340 via Bluetooth interface 728. Additionally, in the same embodiment, the local controller 724 can receive (through the Bluetooth interface) feedback information from the tablet computer 340 about the correct "locator search" direction for the currently selected/active marker. This information can be displayed, for example, by means of some LED array indicator 730 deployed for example around the tip of the hand-held locator 330.

In this example embodiment, the processor or tablet computer 340 can perform the following functions:
1. Initiate and orchestrate the creation/editing subroutines needed to populate the marker pre-implantation database, including barcode scanning of the marker packages;
2. Conduct pre-operation system tests (check and verification of all system components, i.e., pad 320 and locator 330). These tests can significantly improve readiness of the system;
3. Perform real-time control of the system for successful localization of one or more markers during the surgical procedure(s);
4. Process and analyze the results of the localization process (stored in the database) post-surgery.

The processing unit 340 can be a personal computer, tablet computer, personal digital assistant (PDA), smartphone, or similar portable device. These terms can be used interchangeably and the term tablet will be used as a representative term for this group. An example of a tablet computer 340 can be an iPad manufactured by Apple Computers. Alternatively, the tablet 340 can be based on the Android operating system. The tablet 340 can be controlled via its touch-screen and may operate in several modes.

Tablet 340 may execute a plurality of software programs associated with the marker localization system/process. The programs can be used to control the system, to guide the surgeon towards a relevant marker 100, and to calculate the distance from each implanted marker to the locator 330, in real time. In addition, the tablet can be used as a man-machine interface (MMI) for communicating with the surgeon, via audio signal and 2D visual display, etc. Some examples of the software programs are disclosed below in conjunction with FIG. 8-11. The tablet 340 can communicate with the pad 320 and the locator 330 via the Bluetooth communication protocol and hardware stacks. The system is not limited to detecting a finite number of markers. For example, six or more (as an arbitrary number) markers coexisting within an anatomical body of tissue can be simultaneously processed and detected by the system.

Figure 8:
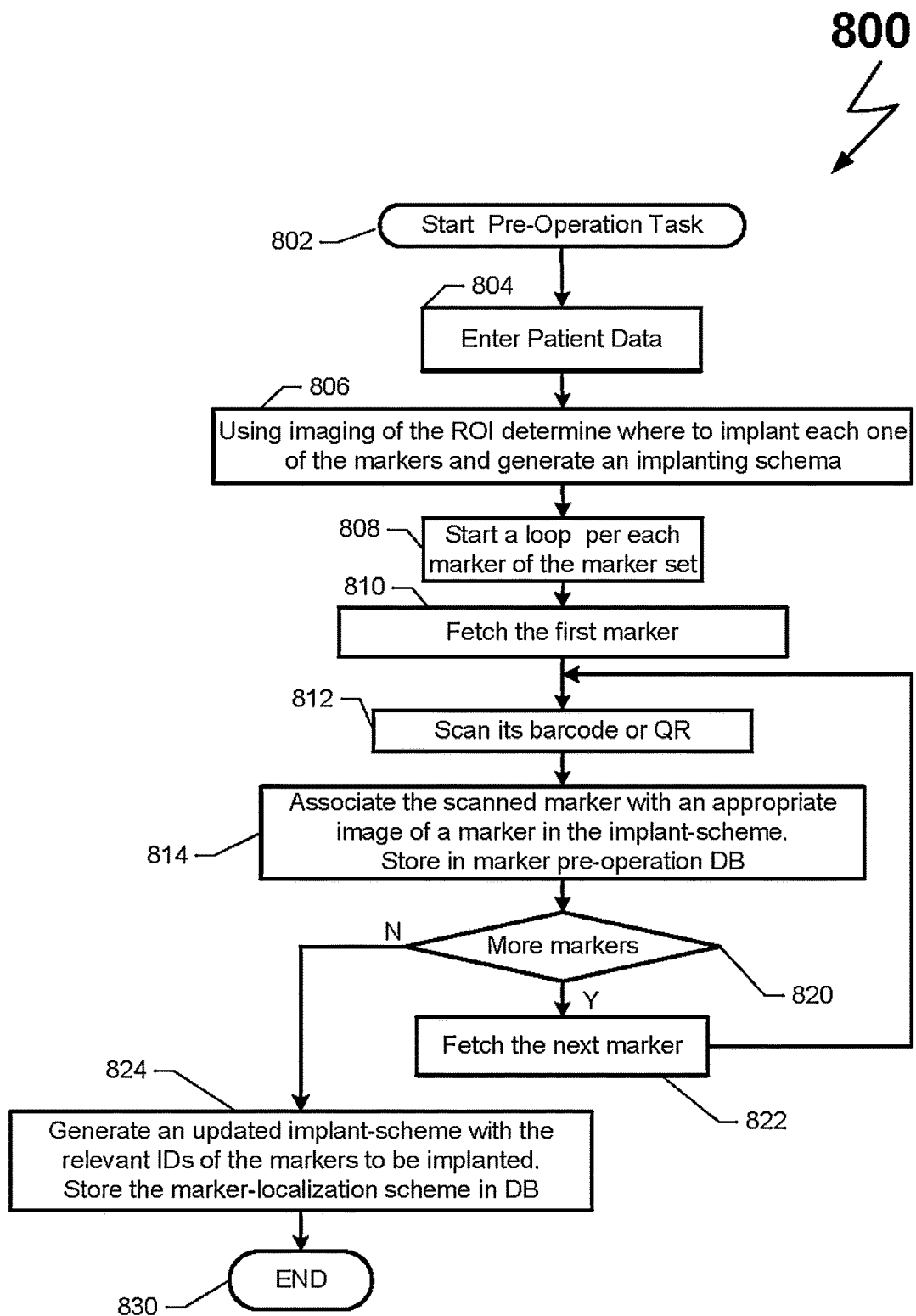
FIG. 8 Illustrates an example of a pre-operational program executing on the tablet computer, responsible for creating the pre-operational marker database used in future medical tasks.

FIG. 8 illustrates a flowchart 800 showing relevant processes that can be implemented during a pre-operation (i.e., pre-surgical) task. Upon initiation 802 of the pre-operation task, the tablet 340 (FIG. 3) can prompt the operator 804 to enter the patient data. The data may include identification and medical details about the patient, information about the surgery, the number of markers to be used, the unique electronic and the unique collective ID of each marker, the ROI, etc.

Next, the operator may plan 806 the surgery. By placing a diagram of the ROI (for that patient, for that particular procedure) on the tablet screen, the operator may determine where to implant/place each of the markers and accordingly may place 806 an image of each marker in the appropriate location related to the image of the ROI generating an implant-schema.

Once the implant schema is complete, a loop from block 810 to 822 can be started. Each cycle in the loop can be associated with one of the markers that appears in the implant-scheme. At block 810, a first marker is fetched and its barcode or QR, which constitutes the marker ID, can be scanned 812 by a camera of the tablet. Then the scanned ID can be associated with the ID of the diagram of the relevant marker in the implant-schema and the association of the two IDs can be stored 814 in a pre-operation DB. The marker can then be placed or implanted (not shown here). It should be noted that the term implantation is used generally and is understood to include placement, attachment etc. of the marker to tissue by any means. The placement of the markers can be via an introducer needle with a plunger whereby single, multiple or sequential markers can be placed at one time. The placement (and detection/localization) of markers can be via an endoscope, laparoscope, robot or video assisted device etc.

Next, a decision is made 820 whether further markers require implantation. If 820 further markers require implantation, then the next marker can be fetched 822 and process 800 loops back to block 812. If 820 there are no additional markers, then at block 824 process 800 can be configured to update the implant-scheme with the ID of the relevant deployed markers. The updated implant-schema with the scanned ID of the markers can be referred to as the Marker-Localization schema and be stored in the DB, to be used for locating the markers and ROI during the surgery. Then process 800 can be terminated 830.

In some potential embodiments of the disclosed technique, the marker-localization schema may comprise an image of the ROI and the location of each marker around the ROI, wherein each marker is presented with its own unique ID. Further, the schema may diagrammatically present the relative orientation and distance between the markers. In some embodiments the schema may include the order of suggested marker localization, for example to start by localizing marker ID #3, and thereafter marker ID #5, etc. Furthermore, some example embodiments of the disclosed technique may present a 3D rendered image on the display of the tablet 340 (FIG. 3), which can be rotated according to the corresponding movement(s) of the locator 330 (FIG. 3).

Figure 9:
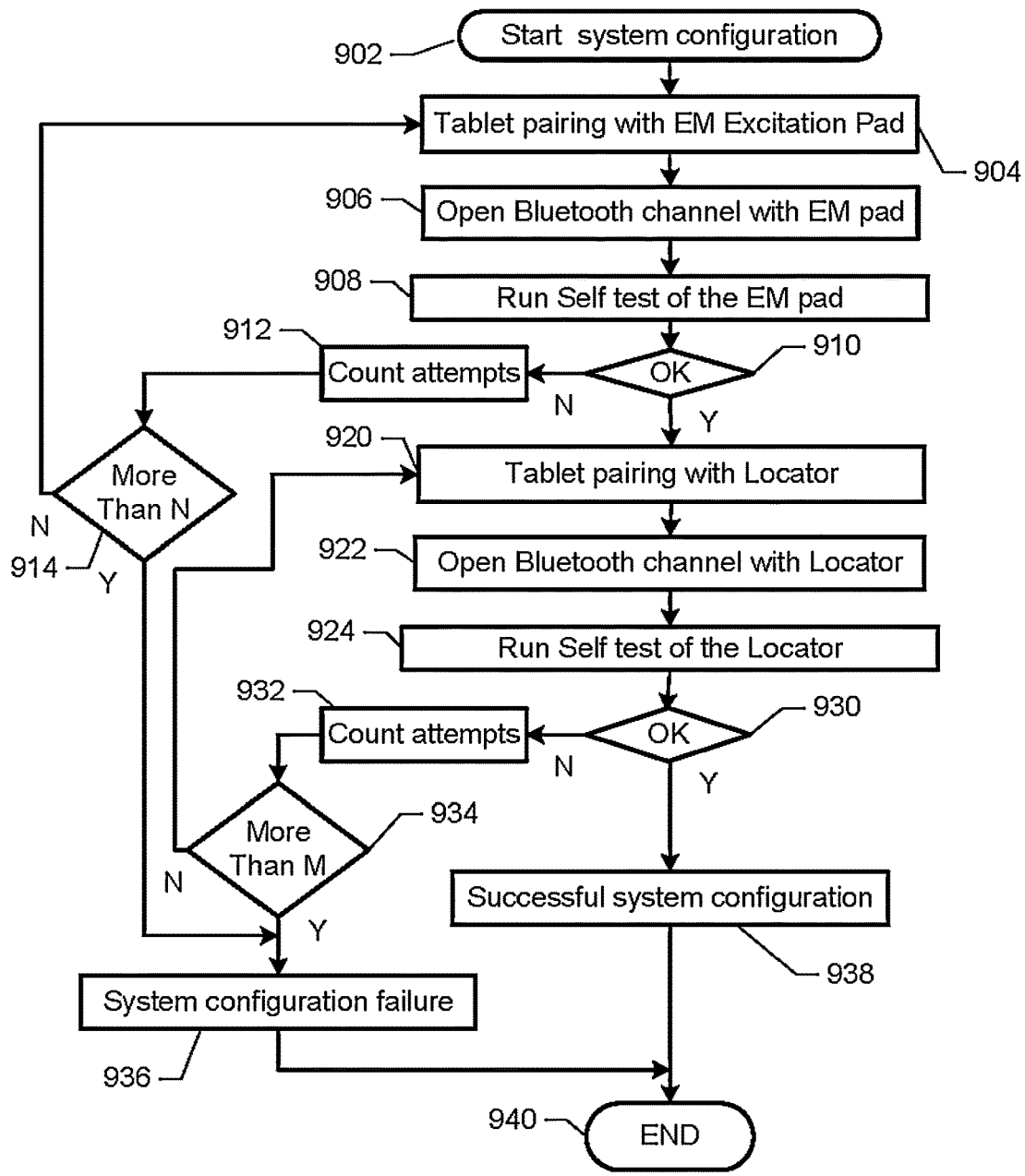
FIG. 9 Illustrates an example of using the tablet computer for pre-operation device testing, to validate system readiness for surgery.

Referring now to FIG. 9 which illustrates a flowchart 900 showing relevant processes that can be implemented upon starting 902 the system for delineating the position of a specific marker/s and hence the ROI within a body tissue. In block 902, two counters, which participate in this process, can be reset. At block 904 the tablet 340 (FIG. 3) can be associated with the pad 320 (FIG. 3) through the pairing process provided by the Bluetooth protocol/chipset. At block 906 a Bluetooth channel with the EM pad 320 can be opened.

Next, the tablet 340 can instruct the excitation pad 320 to execute 908 the self-test of the pad. At the end of the self-test, a decision is made 910 whether the self-test was successfully performed. If 910 no, then a first counter, which counts the number of attempts, can be incremented 912 by one and a decision is made 914 whether the number of attempts is more than 'N' attempts. Typically, 'N' can be an integer number between three to five three, for example. If 914 the number of attempts is not more than 'N', then process 900 returns to block 804.

If 914 the number of attempts is more than 'N', then process 900 may proceed to block 936 and inform the surgeon that the system configuration/set-up has failed and process 900 can be terminated. Some embodiments of the disclosed technique may display the failed elements/subsystems detected within the pad 320 (FIG. 3).

Returning now to block 910, If 910 the self-test of the pad was successfully performed and completed, then locator 330 (FIG. 3) can execute its own self-test. At block 920, the tablet 340 (FIG. 3) can be associated with the locator 330 (FIG. 3) through the pairing process provided by the Bluetooth protocol/chipset. At block 922 a Bluetooth channel with the locator 330 can be opened.

At the end 924 of the self-test, a decision is made 930 whether the self-test was successfully performed. If 930 no, then a second counter, which counts the number of attempts, can be incremented 932 by one and a decision is made 934 whether the number of attempts is more than 'M' attempts. Typically, 'M' can be an integer number between three to five, four, for example. If 934 the number of attempts is not more than 'M', then process 900 returns to block 920.

If 934 the number of attempts is more than 'M', then process 900 may proceed to block 936 and inform the surgeon that the system configuration/set-up has failed and process 900 can be terminated 940. Some embodiments of the disclosed technique may flag the locator 330 (FIG. 3) as the failed element. Returning now to block 930, If 930 the self-test of the locator was successfully completed, then a message can be displayed on the tablet 938 informing the surgeon that the self-test of the system was successfully executed and process 900 can be terminated 940.

Figure 10:
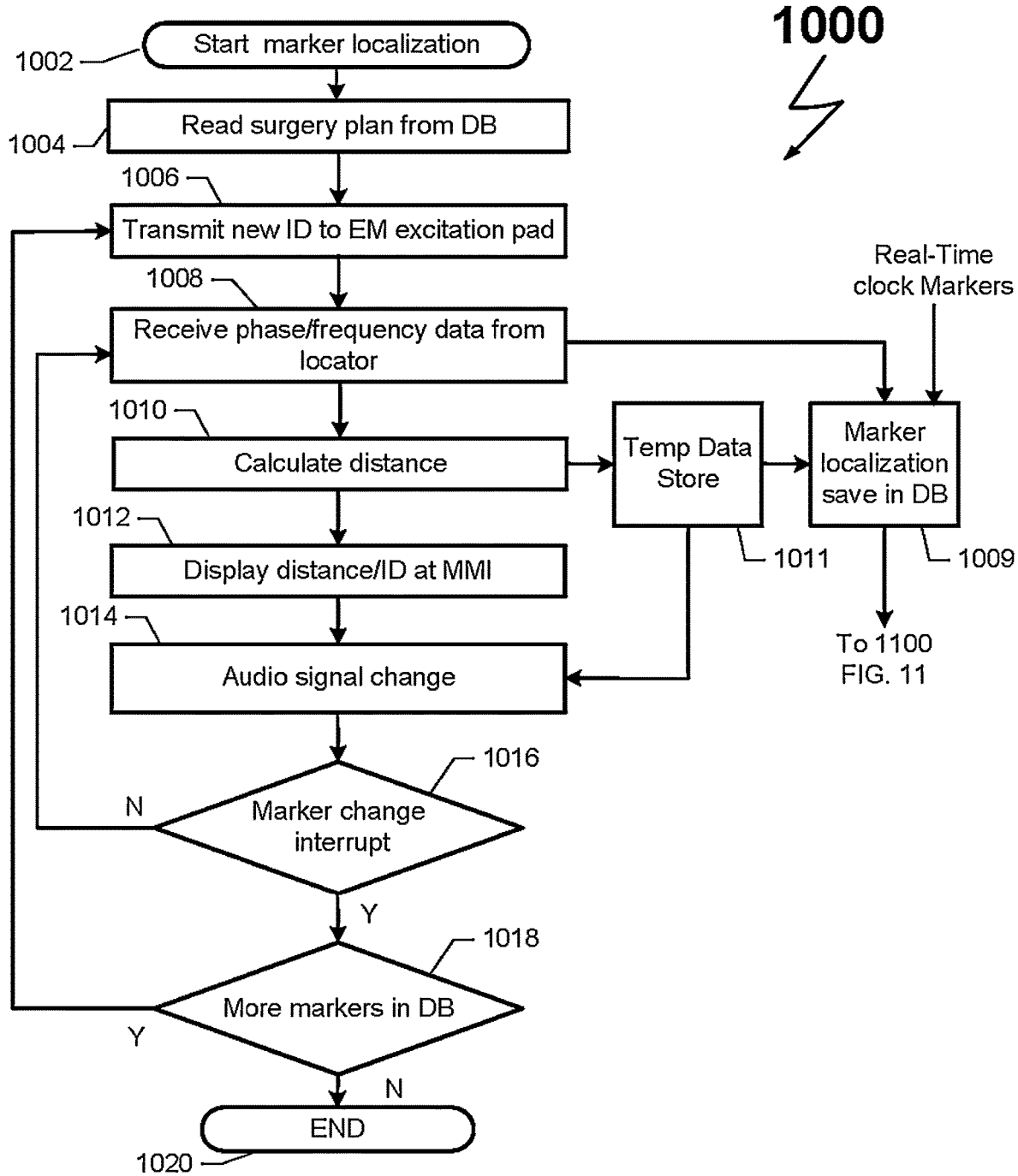
FIG. 10 Illustrates an exemplary flow-chart of the program for marker localization during the surgery.

FIG. 10 illustrates a flowchart showing relevant processes that can be implemented prior to and during an operation, for an example method 1000 employed to guide a surgeon to one or more implanted markers. Upon initiation 1002 the method 1000 may fetch 1004 the Marker-Localization-schema (from Surgery Plan DB), relevant to the current operation. Based on the Marker-Localization-schema, the ID of the first marker is fetched 1006 and appears on the tablet screen. Next, at block 1006 the tablet 340 (FIG. 3) may instruct, via Bluetooth, the pad 320 (FIG. 3) to emit an excitation electromagnetic field 310 (FIG. 3) within the 13.56 MHz band permeating the ROI of the patient 300 (FIG. 3). The electromagnetic field 310 can be BPSK modulated, wherein the modulation reflects the ID of the relevant marker 100 (FIG. 3), thus activating only the relevant marker. Simultaneously, the locator 330 transmits a MW test signal, receives a MW response signal from the activated marker 100 and performs the phase difference measurement.

The Tablet computer 340 receives the Phase/Frequency Data 1008 from the Locator and calculates the distance 1010 between the active marker and the locator. The value of the phase difference and corresponding calculated distance of this specified marker together with the Real-Time Clock Marks is saved (accumulated) in appropriate files of the database 1009. After some predetermined number of marker distance estimates, data will be accumulated in the file allocated for specific marker measurements, and the routine 1100 (Marker direction estimation program) can be initiated. Simultaneously the estimated distance and active marker ID can be displayed 1012 on the computer 340 screen by means of the Tablet-on-screen MMI and the Tablet-generated audio signal 1014 can change its pitch. If the marker-change-interrupt 1016 has not been received the marker localization process can be continued.

Next, a decision is made whether 1016 a marker-change-interrupt was received from the locator. If 1016 no, method 1000 returns to block 1008 for calculating the current distance between the locator and the relevant marker. If 1016 yes, then a decision is made 1018 whether there are more markers in the marker-localization-scheme. If 1018 yes, then the ID of the next marker in the marker-localization-scheme is fetched 1006 and method 1000 returns to block 1006 for handling the next marker. If 1018 there are no more markers in the marker-localization-scheme, then method 1000 can be terminated.

Figure 11:
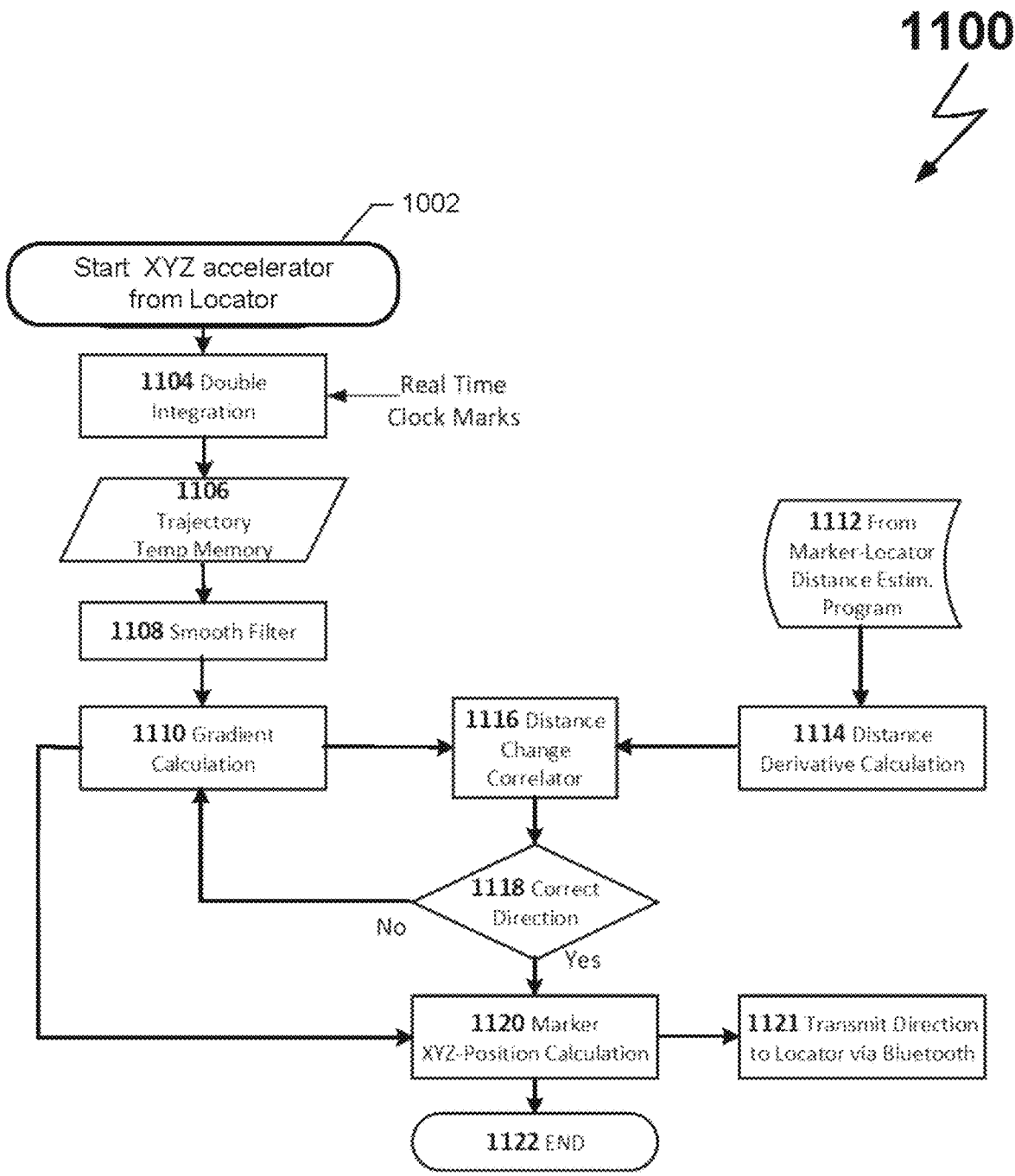
FIG. 11 Illustrates an exemplary of a flow-chart of the marker local direction estimation program.

In the embodiment currently disclosed, FIG. 11 illustrates an example marker direction estimation program 1100 of the tablet computer 340. The program can be initiated automatically or by some method of instruction pre-programming. In an automatic regime, after accumulating some data (i.e., some specified value) in marker distance file 1112, the computer begins accumulating the XYZ-accelerometer data 1102 from the locator 330. After double integration in time 1104, this data is stored in temporary memory 1106 as a trajectory of the locator 330 movement on the surface of the patient's skin. After time-smoothing the trajectory data by the filter 1108, the spatial gradient 1110 of the trajectory is calculated. This gradient is compared with the result of the distance derivative calculation 1114 by means of the distance change correlator 1116. If the gradient and distance change are correlated, the decision about correct direction 1118 is accepted. Next, the tentative 3D position of the active marker can be calculated 1120. The result of "correct direction" angle (based on attitudes provided by gradient calculation 1110) is transferred to the locator 330 via the Bluetooth interface. This direction can be displayed by using the LED array indicator 730 (FIG. 7). The indication of the "correct" direction to the active marker can guide the surgeon to moving the locator 330 in expediting localization of the active marker 100. The localization information belonging to the active marker, for example; the current locator to marker distance; marker ID; direction to the marker; can be displayed on the screen of the tablet computer 340.

Turning to FIG. 4, a schematic of potential RF and MW signal paths is shown for estimating the distance from the marker 100 to the locator 330. Assuming the current distance from the center of the excitation (and synchronization) pad 320 and locator 330 as $R_0$, distance from the center of pad 320 to the marker 100 as $R_1$, and the distance from the marker 100 and the locator 330 as D, the complex amplitudes of the signals received by the marker 100 and the locator 330 can be presented as the following: $S_m=A_1\exp(-i2\pi R_1/\lambda_1)$ and $S_L=A_0\exp(-i2\pi R_0/\lambda_1)$ respectively, where $\lambda_1$ is a wavelength of propagating the frequency band of 13.56 MHz in the patient's body 310.

The signal transmitted by the locator 330 toward a plurality of markers has the following spectral components:

$$S_T=A_L\exp(i(\omega_2+\omega_1)t)\exp(-i2\pi R_0/\lambda_1)+A_L\exp(i(\omega_2-\omega_1)t)\exp(-i2\pi R_0/\lambda_1),$$

where $\omega_2$ and $\omega_1$ are angular frequencies of the bands 5800 MHz and 13.56 MHz respectively. The signal responded by the active marker and received by the locator's microwave antenna has three spectral components: $\omega_2$, $\omega_2+2\omega_1$, and $\omega_2-2\omega_1$. After amplitude detection 715 (FIG. 7) and band pass filtering which is tuned to 27.12 MHz band ($2\omega_1$ frequency) the low frequency signal is proportional to $\cos(2\omega_1(t-2D/v_2-R_0/v_1))$, where $v_2$ and $v_1$ are velocities of the EM wave propagation in tissue for frequencies of $\omega_2$ and $\omega_1$ respectively. The phase difference measured by phase detector 720 (FIG. 7) allows the distance estimation according to the formula $D=\Delta\phi\lambda_1/(2\pi\sqrt{\varepsilon_2})$, where $\varepsilon_2$ is the permittivity of human tissue (for example breast tissue) and $\Delta\phi$ is the phase difference measured by the phase detector 720.

The described algorithm provides an estimation of the distance between the locator 330 (FIG. 3) and the active marker 100 in the case where the center of the reference (EM field excitation) pad, activated marker and locator all reside on the same direct line (the co-axial case).

The marker can be placed at any location within the volume of tissue 310 (see FIG. 3) irradiated by the pad 320. There can be instances of initial, non-zero (axial) distance and (lateral) offset of the marker relative to the center of the excitation pad. In such instances, in the initial localization process, there can be a large initial distance between the locator and the active marker. During the interactive process of marker localization, as the surgeon moves the locator toward the active marker, the distance discrepancy converges to zero. This process of zero convergence can be represented on the computer screen 340 as a series of concentric circles converging to a dot on the screen as and when the locator reaches a site directly over the active marker.

In the description and claims of the present disclosure, each of the verbs, "comprise", "include", "have", and conjugates thereof, are used to indicate that the object or objects of the verb are not necessarily a complete listing of members, components, elements, or parts of the subject or subjects of the verb.

The present disclosure has been described using detailed descriptions of embodiments thereof that are provided by way of example and are not intended to limit the scope of the invention. The described embodiments comprise different features, not all of which are required in all embodiments of the invention. Some embodiments of the present invention utilize only some of the features or possible combinations of the features. Many other ramifications and variations are possible within the teaching of the embodiments comprising different combinations of features noted in the described embodiments.

It will be appreciated by persons skilled in the art that the present invention is not limited by what has been particularly shown and described herein above. Rather the scope of the invention is defined by the claims that follow.

We claim:

1. A system for locating a region of interest (ROI) within a patient's body, comprising:
   one or more markers configured for implantation within the patient's body so as to mark the ROI;
   a pad configured to transmit an electromagnetic reference signal toward the patient's body, the reference signal being configured to activate a selected one of the markers without activating others of the markers;
   a locator configured to:
   receive the reference signal,
   transmit a test signal, which is derived from the reference signal, into the patient's body, such that the activated marker receives the test signal and transmits a response signal derived from the test signal, and
   receive the response signal; and
   a processing unit configured to calculate a distance from the locator to the activated marker based on a phase difference between the response signal and the test signal or between the response signal and the reference signal.

2. The system of claim 1, wherein the locator is configured to derive the test signal from the reference signal by double-balance modulation of a continuous wave carrier signal with the reference signal.

3. The system of claim 1, wherein the locator is configured to determine the phase difference and to deliver the phase difference to the processing unit.

4. The system of claim 1, wherein the markers comprise respective transponders configured to receive the test signal and transmit the response signal.

5. The system of claim 1, wherein each of the markers is configured to derive the response signal from the test signal by double-balance modulation of a continuous wave carrier signal with the test signal and the reference signal.

6. The system of claim 1, wherein the test signal and the response signal occupy a 5.8 GHz band.

7. The system of claim 1, wherein two of the markers are joined to one other by an antenna configured to receive the test signal and transmit the response signal.

8. The system according to claim 1,
   wherein the test signal includes two spectral components offset from a central frequency, in respective directions, by a frequency of the reference signal, and
   wherein the response signal includes a spectral component at the central frequency and two side bands offset from the central frequency, in respective directions, by a second harmonic of the frequency of the reference signal.

9. The system according to claim 1, wherein each of the markers is configured to transmit the response signal while simultaneously harvesting energy from the reference signal.

10. The system according to claim 1, wherein each of the markers is configured to transmit the response signal such that the response signal includes a component at a harmonic of a frequency of the reference signal, and wherein the processing unit is configured to calculate the phase difference by scaling phase-shift information in the component.

11. The system according to claim 1, wherein the system is for use with a surgery table, and wherein the pad is configured for placement on the table below the patient's body.

12. The system according to claim 1, wherein the pad comprises an antenna configured to transmit the reference signal by generating an electromagnetic near field that covers an anatomical volume containing the ROI.

13. The system of claim 1, wherein, to facilitate selecting any one of the markers for activation, the markers are visually differentiable from each other in an image of the patient's body.

14. The system of claim 13, wherein the image includes an X-Ray image.

15. The system of claim 1,
wherein the markers store different respective ID codes, and
wherein the pad is configured to modulate the reference signal using the ID code of the selected one of the markers.

16. The system of claim 15, wherein the pad is configured to modulate the reference signal using the ID code of the selected one of the markers in accordance with a Binary-Phase-Shift Keying (BPSK) method.

17. The system of claim 1, wherein a carrier frequency of the test signal is higher than a carrier frequency of the reference signal.

18. The system of claim 17, wherein the carrier frequency of the test signal is a microwave frequency.

19. The system according to claim 18, wherein each of the markers comprises a dual-band antenna comprising a first antenna configured to harvest energy from the reference signal and a second antenna configured for microwave interactions.

20. The system of claim 1, wherein the pad comprises a loop antenna configured to transmit the reference signal.

21. The system according to claim 20, wherein the loop antenna is larger than a breast area of the patient.

22. The system of claim 1, wherein the markers comprise respective non-ferrite antennae, and wherein the reference signal provides enough energy to activate the markers via the non-ferrite antennae.

23. The system according to claim 22, wherein the markers do not comprise any ferrite, such that the markers are compatible with magnetic resonance imaging.

24. The system according to claim 1, wherein the processing unit is further configured to locate the activated marker based on multiple distances from different respective points, through which the locator is moved by a user, to the activated marker.

25. The system of claim 24, further comprising two or more LEDs arranged around a circumference of the locator and configured to guide the user in moving the locator.

26. The system of claim 24, wherein the locator comprises at least one XYZ-IMU (Inertial measurement unit) configured to output data as the locator is moved, and wherein the processing unit is configured to locate the points based on the data.

27. The system according to claim 1, wherein each of the markers is configured to use excess energy harvested from the reference signal to amplify the response signal.

28. The system according to claim 27, wherein the excess energy is due to a spectral difference between the test signal and the response signal.

29. A method for locating a region of interest (ROI) within a body of a patient, the ROI being marked by one or more markers implanted within the body, the method comprising:
transmitting an electromagnetic reference signal toward the body, such that the reference signal activates a selected one of the markers without activating others of the markers, and is received by a locator;
transmitting a test signal, which is derived from the reference signal, from the locator into the body, such that the activated marker receives the test signal and transmits a response signal, which is derived from the test signal, to the locator; and
calculating a distance from the locator to the activated marker based on a phase difference between the response signal and the test signal or between the response signal and the reference signal.

30. The method according to claim 29,
wherein the markers store different respective ID codes, and
wherein transmitting the reference signal comprises modulating the reference signal using the ID code of the selected one of the markers.

31. The method according to claim 29, wherein transmitting the reference signal comprises transmitting the reference signal from a loop antenna larger than a breast area of the patient.

32. The method according to claim 29, wherein the markers include respective non-ferrite antennae, and wherein the reference signal provides enough energy to activate the markers via the non-ferrite antennae.

33. The method according to claim 29, further comprising locating the activated marker based on multiple distances from different respective points, through which the locator is moved by a user, to the activated marker.

34. The method according to claim 29, wherein each of the markers is configured to transmit the response signal such that the response signal includes a component at a harmonic of a frequency of the reference signal, and wherein the method further comprises calculating the phase difference by scaling phase-shift information in the component.

35. The method according to claim 29, wherein transmitting the reference signal comprises transmitting the reference signal from below the body of the patient.

36. The method according to claim 29, wherein transmitting the reference signal comprises transmitting the reference signal by generating an electromagnetic near field that covers an anatomical volume containing the ROI.

* * * * *